United States Patent [19]
Borggaard et al.

[11] Patent Number: 5,918,977
[45] Date of Patent: Jul. 6, 1999

[54] METHOD AND PLANT FOR MIXING AND ANALYZING UNHOMOGENEOUS FLOWABLE FOODSTUFF, FODDER OR PHARMACEUTICAL MATERIAL

[75] Inventors: Claus Borggaard, Viby Sj.; Freddy Petersen, Jyllinge; Hilmer Jensen, Skælskør; Jens Havn Thorup, København N, all of Denmark

[73] Assignee: Wolfking Danmark A/S, Slagelse, Denmark

[21] Appl. No.: 08/875,441

[22] PCT Filed: Feb. 9, 1996

[86] PCT No.: PCT/DK96/00065

§ 371 Date: Aug. 21, 1997

§ 102(e) Date: Aug. 21, 1997

[87] PCT Pub. No.: WO96/24843

PCT Pub. Date: Aug. 15, 1996

[30] Foreign Application Priority Data

Feb. 10, 1995 [DK] Denmark ............................ 0155/95

[51] Int. Cl.⁶ .................................................... B01F 15/00
[52] U.S. Cl. ............................................................ 366/140
[58] Field of Search ................................. 366/140, 152.1, 366/151.2, 159.1, 136, 137; 73/61.82, 863.81; 426/231; 356/440, 441, 442

[56] References Cited

U.S. PATENT DOCUMENTS

| | | |
|---|---|---|
| 3,499,499 | 3/1970 | Bilbrough ................................ 366/140 |
| 3,695,763 | 10/1972 | Shiuh ....................................... 356/441 |
| 3,838,926 | 10/1974 | Kato et al. ............................... 356/442 |
| 3,893,811 | 7/1975 | Good et al. .............................. 366/140 |
| 3,972,625 | 8/1976 | Takahashi et al. ....................... 356/442 |
| 4,017,186 | 4/1977 | Shofner et al. .......................... 356/342 |
| 4,102,177 | 7/1978 | Okada et al. ............................ 356/442 |
| 4,171,164 | 10/1979 | Groves et al. ........................ 366/152.1 |
| 4,496,244 | 1/1985 | Ludwig ................................... 366/140 |
| 4,520,651 | 6/1985 | Litman ................................ 366/152.1 |
| 4,692,620 | 9/1987 | Rosenthal ................................ 356/440 |
| 4,844,619 | 7/1989 | Lesar et al. .............................. 366/140 |
| 4,872,353 | 10/1989 | Orr, Jr. et al. ........................... 366/140 |
| 5,247,558 | 9/1993 | Hendrix et al. .......................... 356/441 |
| 5,476,320 | 12/1995 | Taguchi et al. ....................... 366/152.1 |

FOREIGN PATENT DOCUMENTS

| | | |
|---|---|---|
| 2 137 340 | 10/1984 | United Kingdom . |
| WO 81/02467 | 9/1981 | WIPO . |
| WO 83/02158 | 6/1983 | WIPO . |

OTHER PUBLICATIONS

Reichert et al. "Kostenersparnis bei der Fertigung von Wurstwaren durch programmgesteuerte Rezepturoptimierung", Fleischerei–Technik, 1993, vol. 44(6), pp. 438–440, pp. 443.

Primary Examiner—Tony G. Soohoo
Attorney, Agent, or Firm—Pennie & Edmonds LLP

[57] ABSTRACT

The present invention relates to a method of mixing inhomogeneous flowable food material, fodder material, or pharmaceutical material in a tank provided with mixing devices. The method comprises measuring and registering the content of one or a number of components in samples taken from the material in the tank.

23 Claims, 7 Drawing Sheets

METHOD AND PLANT FOR MIXING AND ANALYZING UNHOMOGENEOUS FLOWABLE FOODSTUFF, FODDER OR PHARMACEUTICAL MATERIAL

TECHNICAL FIELD

The present invention relates to a method of mixing inhomogeneous flowable food material, fodder material or pharmaceutical material in a tank provided with mixing devices, said method comprising measuring and registering the content of one or a number of components in samples taken from the material in the tank.

BACKGROUND ART

Minced or comminuted meat, e.g. for use in hamburgers, is traditionally produced from raw materials in the form of meat and fat obtained when processing or trimming carcass cuts and the like. The raw materials are coarsely comminuted down to a particle size of 10–15 mm and are placed in respective tanks or tubs, of which one e.g. contains pure meat and another one fat-containing meat or possibly pure fat. The desired composition of the finished product is provided by mixing the various types of meat and fat raw material in predetermined ratios, so that the mixture will fulfil certain specifications with regard to fat, protein etc. When the correct ratio has been achieved, the raw materials are mixed in the best possible manner without spoiling them by "overmixing". Then, the mixture is discharged from the tank and finally comminuted to the desired particle size, after which the product is used for making hamburgers, sausage meat or other products.

Especially the fat content in the raw materials can vary considerably, and for this reason it is necessary to determine the fat content once or a number of times to ensure that the finished product fulfils the specifications. Either a direct or an indirect method may be used to ensure that the finished product has the specified fat content.

The direct method consists in that the operator, on the basis of her or his experience, will introduce the various types of raw materials in the mixer in proportions estimated to make the mixture contain a surplus of meat. When the ingredients have been mixed, the operator takes a sample that is analysed for fat content. Based on the result of the analysis, the operator adjusts the mixture by adding a calculated amount of fat-containing raw material. After renewed mixing, a new sample is taken and analysed. The result of this analysis will normally fulfil the specifications, so that all that now remains is to complete the mixing process.

The method requires much time and effort to ensure that the finished product complies with the specifications. Even then, the content of the various ingredients in the finished product will vary considerably within the limits of the specifications, so that in may cases, the product will lie relatively far from the optimum. If adjustments and mixing operations have to be repeated too often, problems with so-called "overmixing" can arise, manifesting themselves as formation of fat smears and exudates, impairing the quality of the product. In many establishments, however, the method is preferred, as it is flexible and makes it possible to use the raw materials in their original state and without having to analyse them.

The indirect method consists in that each and every batch of raw materials is analysed for its content of fat, protein and water. In other words: from each and every container or tub containing raw material, samples have to be taken and analysed. After this, the results of the analyses are used to calculate the quantity of each type of raw material to be used for producing a finished product with predetermined specifications. The calculation is preferably carried out using a special computer program, as it may be necessary to use 5–10 different types of raw materials. If all instructions are followed, the finished product will comply with the specifications.

This method tends to be preferred by an increasing number of establishments, as it makes it possible to avoid "overmixing" and to come closer to the optimum composition or to comply with stricter specifications.

With both methods, the fat content is determined by means of one of the usual methods of analysis in the meat-processing industry, of which some are carried out "at line", i.e. by the operator in the processing room, and some "off line", i.e. by an assistant in a separate laboratory. The first type of methods of analysis comprises the determination of fat by means of X-ray (Anyl-Ray) and determination of specific weight (Scanalyser). The latter type comprises wet chemical analysis, Fosslet analysis, NIT-transmission measurement (Tecator) and NIR-reflection analysis.

Both of these methods require the operator to be skilled in taking a sample that is representative of the full amount of material.

U.S. Pat. No. 4,844,619 (Weiler & Co.) discloses a specially designed mixing machine provided with a device for taking samples to be analysed for their fat content. The machine comprises an elongate mixing tub and a worm conveyor placed in a longitudinal recess in the bottom of the tub. The worm serves to move material from one end of the tub to the other end during the mixing process. When the worm rotates in one direction, it can also convey new raw material into the tub, while with the opposite direction of rotation, it can convey a fully mixed meat product out of the tub.

The device for taking samples is placed below the mixing tub and is constructed like a meat mincer with a worm. Meat material from the recess in the mixing tub falls down into the meat mincer, and the latter advances it against a perforated disc with a rotating knife, finally mincing the material to a suitable particle size. When the material in the mixing tub is to be analysed, the meat mincer is started and a suitable quantity of finely minced sample is collected at the end of the mincer. The fat content of the sample is determined in a separate measuring equipment operating by means of X-rays.

With this mixing machine it is not required that the operator is skilled in taking a representative sample. The sample, being automatically taken out and finely minced by means of the meat mincer, should be representative of the material in the mixing tub, because the worm conveyor in the recess in the tub causes the different raw materials to be mixed with each other.

U.S. Pat. No. 4,171,164 (The Kartridg Pak Co.) discloses a system, in which meat without fat and meat containing fat, respectively, are introduced into a mixing tub in proportions giving a certain percentage of fat in the product in the tub after mixing. The system may comprise two separate lines, each advancing a respective type of raw material to the mixing tub.

Firstly, the raw materials are coarsely comminuted to a particle size of 10–15 mm, and are then pumped to respective measuring devices, using dual-energy X-ray for continuously determining the fat content in each type of raw material. After this, the material flow of each type of raw material is measured by means of hopper devices collecting material and acting upon some weighing cells. Finally, the two types of raw material are introduced together in the mixing tub. The percentage of fat in the mixing tub may be computed continuously based on the measuring results. The ratio between the flow of the two material streams is controlled so as to finally achieve a mixture with a predetermined percentage of fat. E.g., the pump in one of the lines can run with a constant output and the pump in the other line with a varying output depending on the instantaneous and integrated measuring results.

The raw materials having been introduced together in the tub are mixed to form a homogeneous mass that is discharged into a hopper and finely minced to the desired product, e.g. sausage meat.

This system requires a considerable quantity of equipment to be provided and maintained. Further, it is based upon the material passing unchanged through the analysis and on measuring all the material. These conditions can only be met by extremely few methods of analysis.

SUMMARY OF THE INVENTION

It is the object of the present invention to provide a method of the kind referred to initially, with which it is possible to determine the content of one or a number of components of a material being mixed in a container by automatically taking and analysing samples, said method also making it possible to determine whether the material in the container has been mixed into a homogeneous mass. It must also be possible to use the method, even if the size of an automatically taken sample is less than the representative quantity required to determine the content of the components with the desired accuracy, said representative quantity when operating with meat products of the types described above usually constitutes 5–10 kg.

The above object is achieved by the method according to the present invention, which is characterized in that material is removed from the tank through a tube situated adjacent to the tank and communicating with the internal space of the tank, the material having been removed is moved to a segment of the tube adapted for making measurements, the effect caused by the material placed in said tube segment on electromagnetic energy made to enter the tube is measured, the above steps a–c, possibly comprising the introduction of completely or partly new material in the tube segment, are repeated once or a number of times, and the individual measurement values or sets of same from the individual measuring procedures are registered.

With the method according to the present invention, it is not only possible to determine automatically the content of components in the material, but at the same time it is also possible to monitor the mixing process and to use relatively small samples, i.e. considerably less than the 5–10 kg required when processing coarsely comminuted meat products. Thus, the method according to the present invention exhibits substantial advantages as compared to the methods used at the present time.

The taking of samples and the analysis of the material in the mixing tank may be carried out automatically. The method does not require operators to be skilled in taking representative samples of the material. The determination of e.g. the fat content in meat products being mixed may take place as often as desired, and every time, the sample is taken from the mixing tank in the same manner, thus contributing to improving the reproducibility. The equipment does only have to be dimensioned for relatively small samples, because the taking and measuring of samples are merely repeated, until the sum total of the measurements is representative and provides the desired accuracy. In other words: the mechanical parts may be small, and the volume of material used for measurement in each cycle may be chosen to be the optimum for the measuring method being used.

The content of components in the material can be monitored during the whole mixing operation by automatic and repeated sampling and analysis, and it is possible to determine when the material has achieved the requisite homogeneity. A novel feature within this field is that the mixing process may be interrupted as soon as the material has been sufficiently and thoroughly mixed.

When carrying out the method according to the present invention it is possible to use the mixing equipment already installed in the establishments. All that is required is to provide them with a device for taking samples and making analysis.

It is clearly an advantage to carry out the analysis directly on the material being mixed instead of on each and every batch of raw material as in the previously known indirect method referred to above. Meat having been processed at other locations in the same establishment can, after being comminuted, be used directly in the mixer without first having to analyse it and keep it separate from other batches. There is also no need for accurate weighing of the quantities of meat introduced in the mixing tank or for use of complicated and costly data-processing programs for adjusting the percentage of fat. Re-examination is unnecessary.

If desired, the raw materials may be introduced a number of times in succession, e.g. if a pre-mix of two raw materials is to be produced first, and then a finished mixture is to be produced by adding a third raw material. This fact may e.g. be exploited if the finished mixture is to contain two components that the measuring method is unable to distinguish from each other. If e.g. a sausage meat with a certain proportion between pork and beef is desired, a pre-mix having the correct ratio between pork and fat may be produced, after which beef and fat can be added until the mixture with the desired composition has been produced.

The method according to the present invention may be used in connection with the mixing of fat-containing meat raw materials, but it is possible to use it with the same advantages with others of the flowable materials referred to, whether these are in the form of particles or liquid.

Materials of interest are e.g.:

vegetable foods, such as wheat, barley, rye, maize, rice, coffee and cocoa in the form of whole grains or milled product (analysis for protein, starch, carbohydrate and/or water), seeds, e.g. peas and beans, such as soya beans (analysis for protein, fat and/or water), products mainly consisting of or made from vegetable raw materials, such as snacks, dough, vegetable mixtures, margarine, edible oils, fibre products, chocolate, sugar, syrup, lozenges and dried coffee extract (powder/granulate), animal foodstuffs, such as dairy products, e.g. milk, yoghurt and other soured milk products, ice cream, cheese (analysis for protein, carbohydrate, lactose, fat and/or water), meat products, e.g. meat of pork, beef, sheep, fowl and fish in the form of minced or emulgated products (analysis for protein, fat, water and/or salts) and eggs, all in more or less frozen condition, fodder, e.g. pills or dry/wet fodder mixtures of vegetable products, fats and protein-containing raw materials, including pet food, pharmaceutical products, such as tablets, mixtures, creams and ointments.

A particular embodiment of the method according to the present invention comprises that the material being present in the tube section during a measurement constitutes a quantity not being representative for determination of one or a number of components of the material in the tank on the basis of a recorded measuring value or set of same, and that the content of one or a number of components of the material in the tank is determined by repeating steps a–d of claim 1 so many times with introducing new material into the tube segment, that the sum total of the quantities of material being successively introduced into and measured in the tube segment constitutes a representative quantity, after which the content of the component or components concerned is computed on the basis of the measuring values or sets of same having been registered.

The sample-taking and analysis should preferably be carried out in a non-destructive manner and allowing the sample material to be returned to the tank unharmed. For this reason, the method of the invention is preferably carried out by the material, which with regard to components and size of any particles is substantially unchanged relative to the material in the tank, being introduced into the tube segment, and that when the measurement has been carried out, said material is returned to the tank at a distance from the opening serving for removing material from the tank.

Advantageously, the method is performed by the removing of material from the tank, the moving of the material having been removed from the tank to the segment of the tube and the measurement of the effect caused by the material on electromagnetic energy is performed while the material is being treated in the tank by means of the mixing devices, whereby it is possible to save time and possibly to facilitate the taking of samples from the tank.

By performing the measurements while the material in the tube segment is at rest, it is possible also to use measuring methods requiring relatively long measuring periods.

Material present in the tube segment and containing air or gas is compressed, preferably to a pressure of between 200 and 2000 kPa (2 and 20 bar), before the measurement is carried out. Hereby air bubbles possibly being present in the material will be compressed or dissolved so as normally to improve the measuring accuracy and simplify the measurement.

For measuring the properties of a sample it is possible to use different types of electromagnetic energy, preferably by the use of electromagnetic energy in the form of microwaves of frequencies in the interval between 300 MHz and 300 GHz, single-energy, dual-energy or multi-energy, X-ray or near-infra-red radiation.

The designation "near-infra-red spectroscopy" (NIR) is used for measuring methods being based upon the interaction between matter and electromagnetic radiation in the wavelength interval from 700 to 2,500 nm. The reason for using this designation is that it covers that part of the infra-red wavelength interval lying closest to the visible spectral interval of 400–700 nm. In the literature, the designation "near-near-infra-red interval" ($N^2IR$) is used for electromagnetic radiation with wavelengths from 700 to 1,200 nm.

Meat consists substantially of water, protein and fat. Each type of chemical bond, e.g. O—H, C—H, C=O, C—N, N—H, absorbs light at wavelengths being characteristic of the particular part of the molecule. The absorption is caused by two different atoms being bonded to each other functioning as an electric dipole receiving energy from the electric and magnetic fields in the radiation, causing the group of atoms to vibrate. The light absorbed by a C=O bond in a triglyceride will have a wavelength differing from that absorbed by a C=O bond in a protein molecule. By measuring the attenuation of light passing through a sample of meat and having one of these characteristic wavelengths it is possible to determine the percentage of a component of the meat.

Measurements in the near-infra-red interval may be carried out in two ways, either by transmitting light through the sample (near-infra-red transmission, NIT) or on the basis of the reflection from the surface of the sample (near-infra-red reflection, NIR). In samples with a high content of water, such as meat, NIT cannot be used with measurements above 1,300 nm, because the absorption in the water molecules is far too high at longer wavelengths. If an Si-detector is used, it is only possible to operate at shorter wavelengths than approx. 1,050 nm, since this type of detector is insensitive at longer wavelengths.

Reflection measurements have the disadvantage of having to be carried out through a quartz-glass window, since ordinary glass does not allow much near-infra-red light to pass through. It cannot be avoided that fat from the coarsely comminuted meat adheres to the inside of the quartz-glass window, thus possibly causing erroneous measurements. Further, a reflection measurement will not be as representative as an NIT-measurement, because the volume being measured is small.

For this reason, optimum conditions for measuring are achieved by carrying out near-infra-red measurements by transmission through a physical path length in the measuring tube of e.g. 50–60 mm. The sample preferably remains stationary during that fraction of a second, during which the measurement is carried out. The sample should be as free from air pockets as possible, and this is achieved by compressing the sample.

The near-infra-red radiation may be detected by using the following materials:

Si: A highly sensitive and cheap type of detector, used in the interval 400 to 1,100 nm.

Ge: Hardly as sensitive as Si, but may be used from 800 to 1,800 nm.

InGaAs: only half as sensitive as Si, but reacts very quickly and may be used from 800 to 1,760 nm.

PbS: Low sensitivity, but is cheap and may be used from 650 to 10,000 nm. Temperature stabilization is required.

PMT (Photo-Multiplier Tube): This is by far the most highly sensitive type of detector.

Measurements on natural products have shown that there is no linear correlation between the absorption of light and the percentage of a compound in the sample. The absorbance is not only due to the presence of absorbent compounds in the sample, but is also influenced by the dispersion of light in the sample. Further, it must be taken into account that the composition of natural products is so complicated, that absorptions caused by different compounds or functional groups overlap each other in the spectrum. For this reason, it is necessary in this connection to use more complicated mathematical models, e.g. neural networks or classical statistical methods, for determining the content of a compound in the sample.

Tests with comminuted meat raw materials on an NIT-analysis instrument have shown that it is possible to determine the three main components fat, water and protein, even in a situation in which they do not add up to 100% due to other additives.

X-rays are electromagnetic radiation that is dispersed and attenuated by interaction with matter. The radiation is produced by an X-ray source consisting of an electron accelerator and an anode, against which the accelerated electrons are made to impinge. With X-rays, the dispersion and attenuation taking place during the passage of the beam of radiation through a substance increases markedly with an increase of the number of electrons in the substance capable of interacting with the radiation. The variation in the interaction is especially marked in the vicinity of particular energies, the so-called "absorption edges".

For a long time, X-rays have been used to measure the composition of a mixture, and absorption spectra for a series of substances are known. The difference between the mass attenuation coefficient for fat (fatty tissue) and protein/water (meat) may be measured at energies from approx. 0 to 100 keV. In this interval, it is possible to use X-rays for determining the percentage of meat and fat in a material.

If possible, single-energy X-ray measuring equipment is preferably used. When the meat product contains air, dual-energy X-ray equipment is used, as the high energy may be calibrated for measuring the specific weight. The measurements may be carried out continuously or based on discrete counts. In both cases it is necessary to use highly collimated radiation, which causes a substantial reduction of the measuring volume. In order to measure a representative volume it is frequently necessary to carry out a very great number of measurements.

It may be advantageous to carry out measurements with successively changing energies in order to increase the dynamic range and contrast of a system for measuring fat.

X-ray windows may consist of a light material, e.g. epoxy. The capacity of an individual measurement with an X-ray window of maximum size may be 150 cm$^3$.

Microwaves are electromagnetic waves behaving as if consisting of electrical (E) and magnetic (H) waves. The depth of penetration and propagation velocity of the waves are different in different substances. This difference is exploited for measuring components of foodstuffs. When measuring according to these methods, the energy level is so low that the sample is only slightly heated.

At the present time only one apparatus capable of measuring the fat content in comminuted meat is known. This apparatus has been developed by Torry Research Station in Scotland and is adapted to measure the attenuation of microwaves transmitted along the surface of the meat.

In an as yet not published series of tests with a microwave measuring apparatus using transmission measurement, the fat content in trimmings having been coarsely comminuted down to 3 and 10 mm have been measured over a vide range (4–83% fat). The samples were placed in a rectangular waveguide, and the transmission examined using microwaves in the range 1.7 to 2.6 GHz. It turned out to be possible to measure the content of meat and fat using three different measuring principles: Attenuation, phase shift and time delay. A substantial advantage of using transmission measurement as compared with surface measurement is the possibility of using a relative large measuring volume.

By combining an attenuation measurement with a phase-shift measurement it is possible to provide a method that is insensitive to variations in the specific weight of the samples. This means that air bubbles in the sample can be ignored. A time-delay measurement is advantageous if the dispersion of the waves is unknown, the measurement being carried out on the direct wave between the transmitter and receiver through the measuring object. The time delay to the front edge of a received pulse may be measured according to principles known in the field of radar technology.

Microwaves may be unsuitable for measuring frozen or partly frozen meat products, because the water molecules are unable to rotate when in the solid state (ice). For this reason, microwaves are hardly influenced by frozen products.

When carrying out the method according to the present invention, the influence of the material on the electromagnetic energy is preferably measured by measuring the attenuation, phase shift or time delay of the microwaves in the tube segment in the shape of a microwave waveguide, by measuring the attenuation of X-ray radiation transversely through a material contained in the tube segment, or by measuring the transmittance or absorbance of a material contained in the tube segment in the near-infra-red interval (NIT).

It is especially preferred that the transmittance or absorbance of the material placed in the tube segment is measured at a number of wavelengths in the interval between 700 and 2400 nm, especially between 700 and 1200 nm, after which the content of one or a number of components of the material is determined on the basis of the measuring values or sets of same having been registered.

It has been found that NIT-measurement can be used for determining the particle size in the material in the tube. If wanted, the transmittance or absorbance of a particulate material positioned in the tube segment may accordingly be measured at several wavelengths in the range 700 to 2400 nm, especially 700 to 1200 nm and the particle size of the material is determined on the basis of the measuring values or sets of same having been recorded.

A special application of the method according to the invention comprises that the measuring values or sets of same are used to ascertain whether or when the mixture in the tank is sufficiently homogeneous to allow the mixing process to be terminated and the material possibly discharged from the tank or subjected to a succeeding processing step. This makes it possible to avoid problems with so-called "overmixing".

An embodiment of the method of the invention may be utilized for adjusting the composition of the material in the mixing tank. This embodiment consists in that the content of one or a number of components of the material is determined on the basis of the measuring values or sets of same having been registered, and that the results or their deviation from desired values or information about the need for adding material with a view to augmenting the content of a component of the material in the tank to achieve a desired value is/are shown on a display unit and/or used for controlling a dosage control unit associated with the tank and adapted to add a deficit quantity of a component to the material in the tank.

A particularly preferred embodiment of the method according to the invention comprises that the transmittance or absorbance of a particulate material, e.g. a comminuted meat product with an average particle size between 2 and 30 mm, is measured at a number of wavelengths in the near-infra-red interval, preferably between 700 and 1200 nm, after which the measuring values or sets of same having been registered are used to determine the content of one or a number of components of the material, e.g. in a meat product preferably its content of fat, protein, collagen and/or water, and/or to ascertain whether or when the mixture in the tank with regard to one or a number of components is sufficiently homogeneous to allow the mixing process to be terminated and the material possibly discharged from the tank or subjected to a succeeding processing step.

This makes it possible to control or determine a number of different parameters of substantial importance for a satisfactory mixing process.

The present invention also relates to a plant for mixing an inhomogeneous flowable food material, fodder material or pharmaceutical material, and comprising a tank for the material provided with mixing devices, the plant being characterized by further comprising, situated adjacent to said tank, an examining unit comprising a tube having an opening communicating with the internal space of the tank for removing material from the latter, in said tube, a conveying member 18 for conveying material having been removed through said opening into a segment of said tube adapted for carrying out measurements, a measuring device situated adjacent said segment of said tube and adapted to transmit electromagnetic energy into said segment and to measure the influence on this energy exerted by the material being present in said segment, a control unit to cause the measuring procedure comprising the introduction of completely or partly new material in said segment and measuring of its influence on electromagnetic energy, to be repeated, and a recording unit connected to said measuring device and adapted to record individual measurement values or sets of same for material having been measured in the respective measuring procedures.

The measuring device preferably comprises a light source on one side of said tube segment and a light receiver on the opposite side, and that the walls of the tube segment lying in the path of rays between the light source and the light receiver consist of a material that is at least translucent for the wavelength interval of the light to be examined, depending on the flowable material, on which measurements are to be carried out.

An embodiment of the plant is characterized in that the light source and the light receiver are of the wide-spectrum type, and that a rotatable filter disc is placed in the ray path between the light source and the light receiver, said filter disc having a number of filters situated at equal distances from the axis of rotation of the disc and each adapted to allow rays of a respective wavelength interval to pass, a motor on the shaft of said disc being adapted to bring one filter at a time into the path of rays.

A preferred embodiment consists in that a number of monochromatic light sources, each adapted to emit light in a respective wavelength interval, is situated on one side of said tube segment, and that a light receiver is situated on the opposite side of said tube segment.

Hereby between 4 and 20 monochromatic light sources in the form of laser diodes may be situated on one side of said tube segment and adapted to emit light, each in a respective wavelength interval within the region between 700 and 1200 nm.

Further, the present invention relates to an apparatus for taking samples for use in the plant according to the invention in connection with the examination of a flowable material. The apparatus is special by comprising a tube comprising an opening for receiving the material to be examined and a tube segment adapted for carrying out the examination, a movable closure member situated in said tube close to the opening for receiving material, and a conveying member to convey material having been received into the tube segment adapted for carrying out of the examination. Using such an apparatus, it is possible to take a sample directly out of the mixing tank and place it in the measuring space of an analysis equipment.

The closure member may be adapted to be opened in connection with the reception of material and to be closed in connection with the conveying of material having been received into said tube segment adapted for carrying out the examination. This embodiment prevents the material from flowing backwards.

The apparatus may comprise a second closure member in the tube on the side of said tube segment opposite said receiving opening, said second closure member being adapted to be closed for a period while the conveying member conveys fully or partly new material into said tube segment adapted for carrying out the examination, and to open when the material having been examined is to be moved out of said tube segment. Hereby it is possible to compress the material during the measurements and to express it from the measuring region when the measurement has been carried out.

Preferably said conveying member is a plunger slidable in a fluid-tight manner along the inside of said tube. Hereby the smear problems known from worm conveyors, which can give a film of fat on the windows which is disturbing for the measurement, are prevented to a high degree.

Preferably the apparatus comprises one or a number of pneumatic cylinders with associated pistons adapted to actuate said conveying member and/or closure members in said tube.

As mentioned, it has been found that the particle size of flowable material may be determined using NIT measurements. For this reason it is also possible, if so desired, to carry out a particle-size determination, by measuring the transmittance or absorbance of a sample of the material placed in the tube segment at a number of wavelengths in the near-infra-red range (NIT), and to determine the particle size of the material by comparing the set of measuring values having been obtained with corresponding data sets for materials with a known particle size or by inserting the measuring value set in an algorithm provided on the basis of data sets for materials with known particle sizes.

Thus, it is e.g. possible to determine the particle size of a material in a mixing tub or tank or to determine whether two raw materials having different particle sizes have been mixed sufficiently thoroughly.

The representative quantity necessary for determining the percentage of a component, e.g. fat, can vary with the size of the particles. When the particle size is known, it is possible to calculate the representative quantity, and based on this value it is possible to determine how many times the sampling and measuring cycle of the method according to the invention is to be repeated in a plant, in which only small quantities at a time are being examined. In this manner it is possible to carry out the measuring procedure in the shortest possible time with a given accuracy, also in those cases, in which the particle size of the material varies considerably.

The measurements of the particle size may be repeated on fully or partly new material being placed in the tube segment, and the value of the particle size or of the deviation of the measurements from a predetermined value having been found may be utilized for continuous control or monitoring of a machine comminuting or grinding the material. In this manner it is possible to use the measurements for dynamic control of various processes.

It is possible to carry out measurements at a number of wavelengths in the near-infra-red range between 700 and 1,200 nm. This is preferred when working with meat products containing fat.

BRIEF DESCRIPTION OF THE DRAWINGS

In the following detailed portion of the present description, the invention will be explained in more detail with reference to the drawings, in which.

DETAILED DESCRIPTION OF THE PREFERRED EMBODIMENTS

Figure 1:
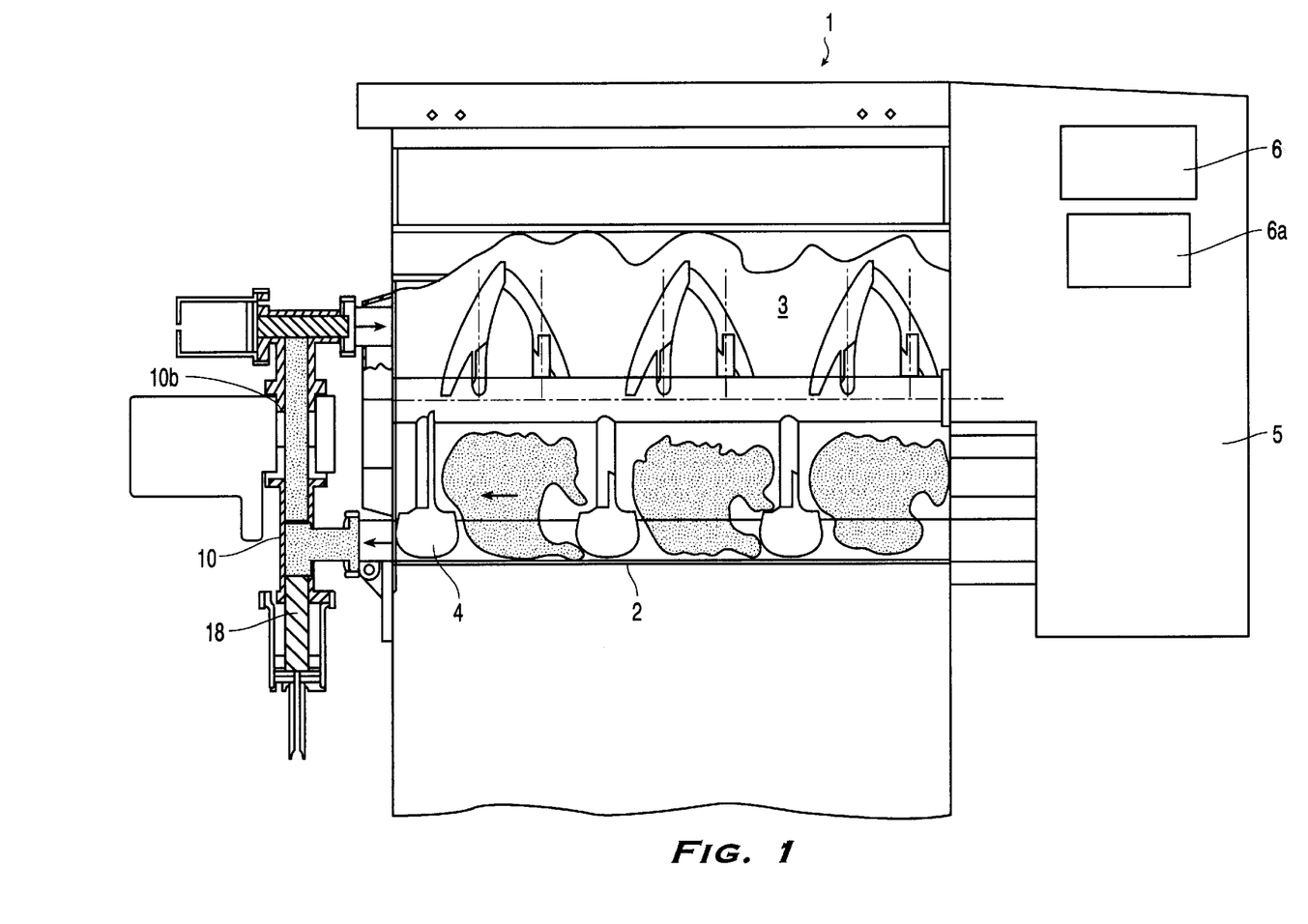
FIG. 1 shows an embodiment of a plant according to the invention seen in elevation and partly in section.

The plant of FIG. 1 comprises a conventional mixer 1 with a mixing tank 2 capable of accommodating between 1,200 and 4,500 kg meat material according to need. In the tank 2 there are two mixing devices consisting of two mutually parallel shafts 3 with radial rods carrying blades 4. The mixing devices can be rotated in both directions by means of a motor arrangement 5. The arrangement is controlled by means of a control panel 6, with which an operator selects the mixing program suited for the work in hand.

In the end of the tank 2 opposite to that of the motor arrangement 5 there is a discharge opening equipped with a trap door 7 (FIG. 2) adapted to be opened and closed by means of a pneumatic cylinder 8. The bottom of the tank 2 is indicated with an arched dotted line. During discharge, the material tends to collect in the deeper left-hand part of the tank, here being "shovelled" towards the discharge opening by the mixing device.

Figure 2:
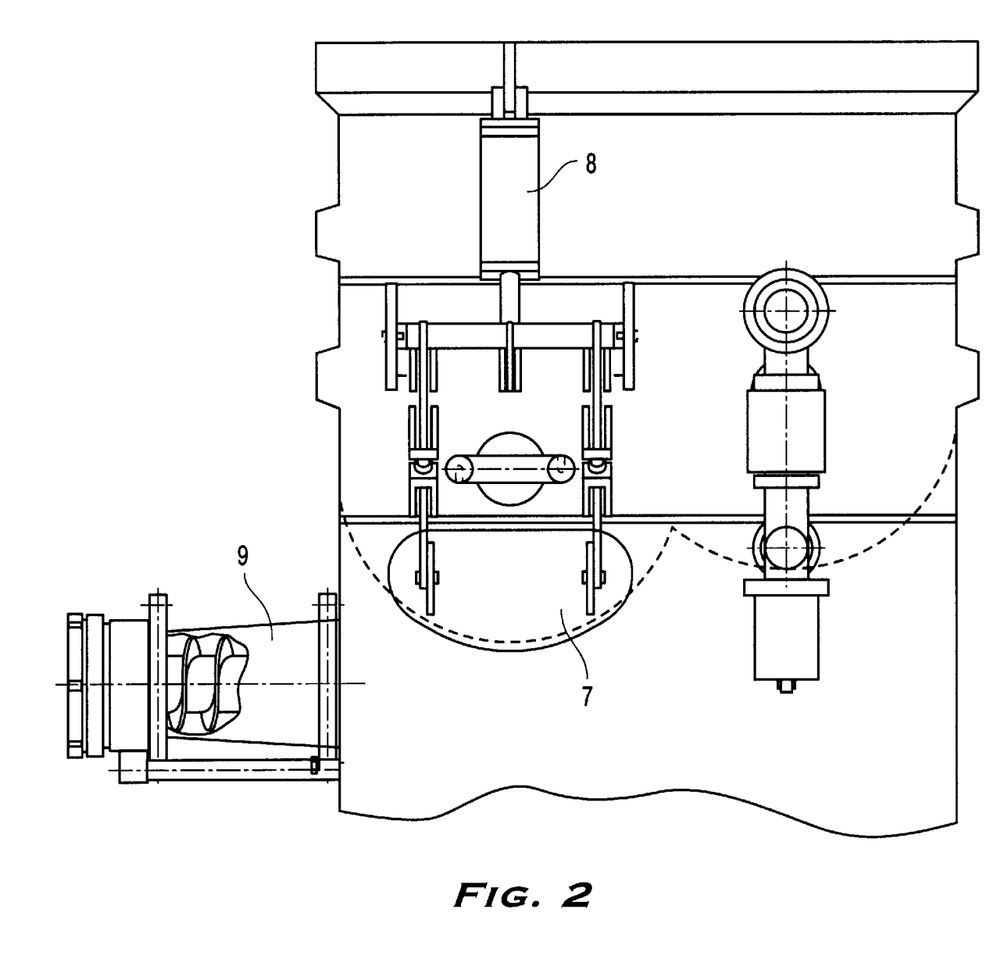
FIG. 2 shows the plant seen from one of its ends.

On one side, the mixing tank 2 carries a worm conveyor 9 constituting an additional facility for discharging material from the tank. The worm conveyor 9 may be terminated in a perforated disc with a rotating set of knives adapted to comminute the material during the latter's discharge. EP-A-0,569,854 (WOLFKING DANMARK A/S) comprises a description of a mixing machine of this type.

In the embodiment being discussed, the tank carries on its wall an apparatus for taking samples from the material in the tank and analysing the samples (FIG. 1). A control unit 6a situated below the control panel 6 is electrically connected to the apparatus. The control unit 6a serves to control the functions of the apparatus and to receive and process measurement data from the apparatus with regard to an automatically taken sample, e.g. in the form of signals expressing the fat content of the sample. Signal-wise, the control unit 6a is connected to the mixer's control panel 6, so that the processed data from the apparatus may be shown to the operator or used for automatic checking and control of the mixing program stored in the control panel 6.

The construction and functioning of the sample-taking apparatus will be evident from FIGS. 3a–3f illustrating various operating positions in a cycle comprising taking a sample from the tank 1 and analysing it.

The apparatus comprises a tube 10 composed of three tube segments 10a, 10b and 10c connected to each other by means of flanges 11. The lowermost and uppermost segments 10a and 10c are angular, so that the tube 10 consists of a vertical central part and two horizontal end parts. In the vertical wall of the tank 2 shown to the left in FIG. 1, an opening is cut close to the bottom, said opening fitting the lower, horizontal end part of the tube, and at a level above the shaft 3 a second opening is cut to fit the upper, horizontal end part of the tube. By means of flanges 12 on the end parts, the tube 10 is secured to the tank 2 opposite the openings, so that material automatically flows into the lowermost tube section 10a and may be returned to the tank by means of a conveying device in the tube.

On the lower tube segment 10a, a cylinder 14, the lower end of which is closed, is secured by means of a flange 13. In the cylinder 14 there are two pistons 15 and 16. The upper piston 15 carries a short tube 17 capable of sliding within a lower, vertical part of the tube segment 10a, while the lower piston 16 carries a plunger 18 having an outside diameter corresponding to the inside diameter of the short tube 17, so that the plunger slides within the short tube. The black areas in FIGS. 3a–3f represent seals providing sealing between mutually relatively movable parts.

A piston rod 19 is secured to the lower side of the piston 16 and protrudes outwardly to the bottom of the cylinder 14. The piston rod 19 comprises a duct 20 for compressed-air and a coupling part 21 for coupling to a compressed-air tube. For the sake of clearness, compressed-air tubes and their connections to control valves are not shown in the figures.

Through the duct 20, air under pressure may be introduced into the interspace between the pistons 15 and 16, causing the piston 15 to be forced upwards. Coupling parts 22 and 23 for connecting compressed-air tubes are also formed in the bottom of the cylinder 14 and in the flange 13 constituting the top of the cylinder, respectively.

The central part of the tube segment 10b serves as a measuring chamber in connection with measurements of the transparency of the meat material to infra-red light of various wavelengths. For this purpose, the tube segment 10b comprises two windows 24 of glass or other transparent material inserted in mutually facing cut-outs in the tube wall. The tube segment 10b carries a housing 25 containing various devices for measuring the transparency of the material at any time being present between the windows 24.

The upper tube segment 10c comprises a flange 26, on which is mounted a cylinder 27 with a closed end. A piston 28 is slidable within the cylinder, and on its right-hand side carries a plunger 29 slidable in the horizontal part of the tube segment 10c. In the closed end of the cylinder 27 there is formed a coupling part 30 for a compressed-air tube, and the flange 26 comprises a similar coupling part 31 for compressed air.

The functioning of the plant will now be described in detail.

Various types of un-analysed raw materials, coarsely minced and then placed in respective storage tubs, are weighed out and placed in the tank 2, in which they are mixed for a short period by rotating the mixing devices. A PLC unit (not shown) controlled by the control unit 6a actuates the valves on the compressed-air tubes connected to the apparatus through the coupling parts 21, 22, 23, 30 and 31 in a manner causing the pistons 15, 16 and 28 to take up the positions shown in FIG. 3a. After this, the mixing devices are made to rotate in such a direction, that the material close to the bottom of the tank 2 is moved towards the opening near the bottom of the tank and is forced out through the opening and into the lower tube segment 10a. In the figures, the material is represented by dotted areas.

When the pressure of the material against the opening is at a maximum, i.e. when a blade 4 is adjacent the opening, the following sampling and measuring procedure is initiated:

Compressed air is admitted to the space between the pistons 15 and 16, causing the piston 15 with the short tube 17 to move upwardly to an upper position, in which the top edge of the short tube 17 abuts against an internal ledge a short distance above the lower, horizontal end part of the tube. In this position, shown in FIG. 3b, the short tube 17 confines the material having been forced into the vertical part of the tube by the mixing devices, the tube already having been closed at the top by the plunger 29.

Now, the material having been confined is compressed by air under pressure being admitted into the space between the bottom of the cylinder 14 and the piston 16 via the coupling part 22, causing the piston 16 with the plunger 18 to move upwardly, thus reducing the volume available to the confined material. At the same time, the volume of the space between the piston 15 and the piston 16 is reduced correspondingly, and the consequent pressure rise being relieved by means of the duct 20 and a back-pressure valve placed on the associated compressed-air tube and set to a predetermined pressure.

During the starting-up of the plant, i.e. when carrying out the first cycle, the vertical part of the tube 10 mainly contains air, for which reason the piston 16 with the plunger 18 will move to an upper position, in which the piston 16 abuts against the lower side of the piston 15. When a few cycles have been carried out, the vertical part of the tube 10 will, however, mainly contain meat material and only a lesser proportion of air. This is the operating situation now to be described.

Figure 3A:
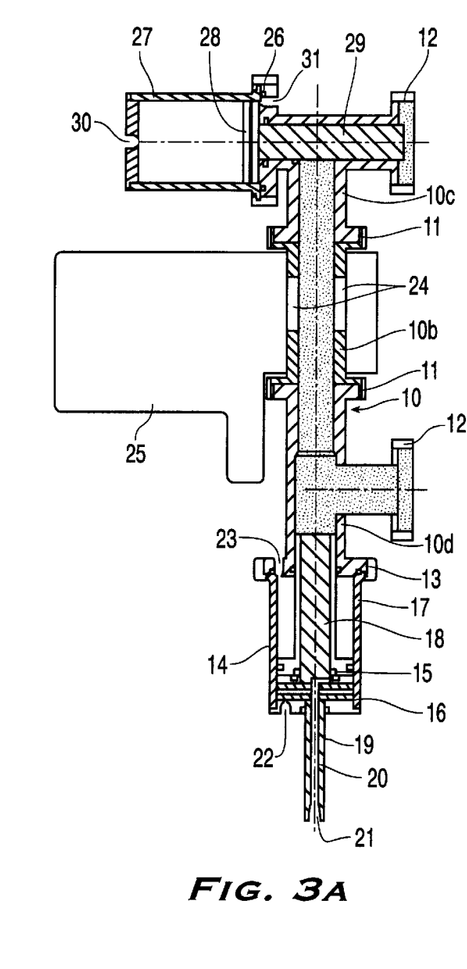
FIGS. 3a–3f show an apparatus used in the plant for automatic taking out samples and analysing these in a measuring equipment, these figures showing the apparatus in various operating positions.
Figure 3B:
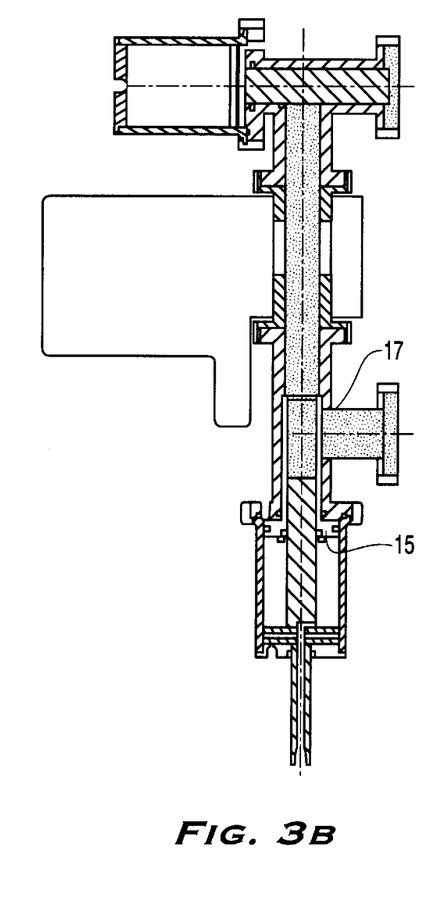
Figure 3C:
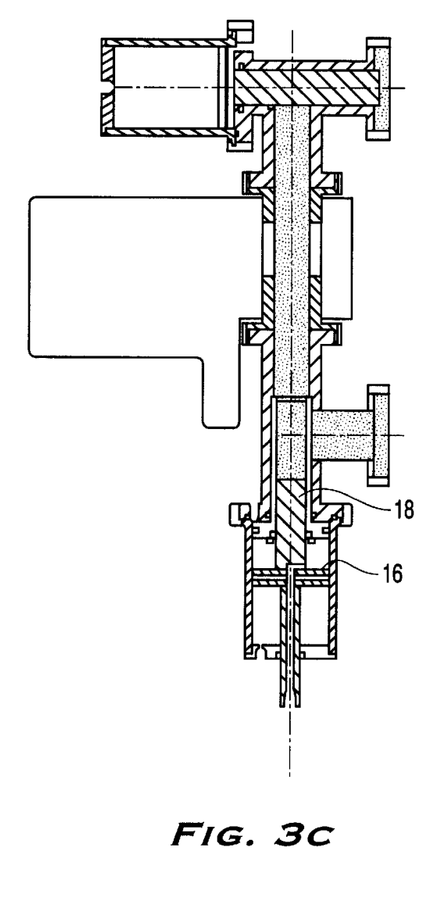

In this operating state, the piston 16 with the plunger 18 will only move to an intermediate position, of which an example is shown in FIG. 3c. In this position, there is equilibrium between the pressure in the confined material and the upwardly directed force exerted by the piston 16. Compression takes place to a relatively high pressure in order to reduce or eliminate the influence of the air upon the measurement being carried out on the material between the windows 24. With the transverse dimensions of the piston 16 and the plunger 18 shown in the drawing, a pressure amplification of five times is achieved, creating a pressure in the material of 1,250 kPa (12.5 bar), if the compressed air is set to a pressure of 250 kPa (2.5 bar).

After this compressing of the material in the vertical part of the tube 10, measurements of the transparency of the material between the windows 24 are carried out at a number of wavelengths in the infra-red region, and the measurement results are used for calculating one or a number of characteristic properties of the material. The construction and the functioning of the measuring equipment will be described in connection with the explanation of FIG. 3d.

When the measurements have been carried out, the pressure in the vertical part of the tube 10 is equalized to atmospheric pressure by moving the piston 28 with the plunger 29 towards the left, compressed air being admitted on the right-hand side of the piston 28 via the coupling part 31. When the vertical part of the tube 10 is opened at the top, material from this tube may expand outwardly in the horizontal part of the tube in the tube segment 10c and further out into the tank 2. As soon as the pressure falls in the vertical part of the tube, the piston 16 with the plunger 18 is moved towards its uppermost position shown in FIG. 3e, causing further material to be discharged from the vertical part and forced out into the tank.

When the piston 28 with the plunger 29 has reached the extreme left-hand position, the piston is reversed towards the initial right-hand position, compressed air being admitted on the left-hand side of the piston 28 through the coupling part 30, the pressure on the right-hand side of the piston being removed at the same time. During the reverse movement, the plunger 29 forces material out from the upper, horizontal part of the tube in the segment 10c and back to the tank 2. In this manner, material having entered the tube segment 10a through the opening close to the bottom of the tank will be returned to the tank 2. During the reverse movement, the plunger 29 will again close the vertical part of the tube 10 at the top as will be evident from FIG. 3f.

After this, the piston 15 with the short tube 17 and the piston 16 with the plunger 18 will be moved towards their bottom positions, pressure being applied to the upper side of the piston 15 via the compressed-air conduit connected to the coupling part 23. During the downward movement of the short tube 17 and the plunger 18 in the vertical tube, the increase in volume creates a sub-atmospheric pressure in the latter. During the final part of the movement of the short tube 17, passage is provided between the vertical tube segment 10b and the lower, horizontal end part in the tube segment 10a, so that material will be sucked into the vertical part of the tube. The opening of this passage will preferably occur at the same time as a blade 4 is opposite the opening near the bottom of the tank, so that at the same time, suction will be applied to the material from one side and pressure from the other. In this manner, new material is moved into the tube segment 10a.

When the pistons 15 and 16 have reached their lowermost position, and the piston 28 is in its extreme right-hand position (FIG. 3a), a portion of material in the vertical part of the tube has been ejected back into the tank and a new portion of material has been taken in from the bottom of the tank for subsequent compressing and measuring in the vertical part of the tube. At this point, one working cycle has been completed. This cycle may immediately be succeeded by new, similar working cycles in a given rythm, e.g. each second (making the cycle time one second). The internal diameter of the vertical part of the tube and the stroke volume of the plunger 18 may e.g. be so dimensioned that each working cycle will move 200–400 ml of new material into the tube. After one or a few working cycles, the new material will have been introduced into the space between the windows 24, after which the measurement may be carried out.

By repeating the measurement on new portions of material being introduced into the space between the windows 24, a sufficient number of measurement data will eventually be obtained to make their sum total representative, making it possible to determine the fat content in the coarsely comminuted material with the requisite accuracy. The quantity of material necessary to achieve representative measurements will depend on the type and particle size of the material. It should be determined for the materials most commonly used, cf. example 1.

Figure 3D:
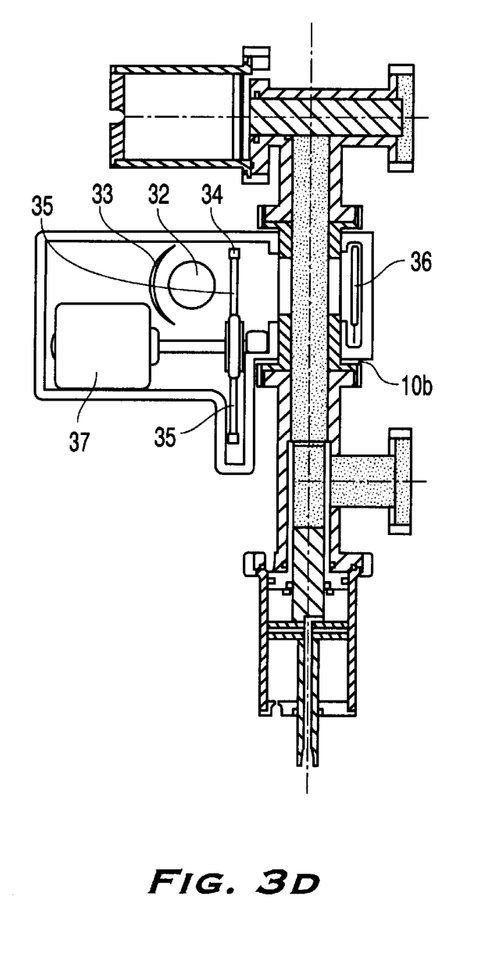
Figure 3E:
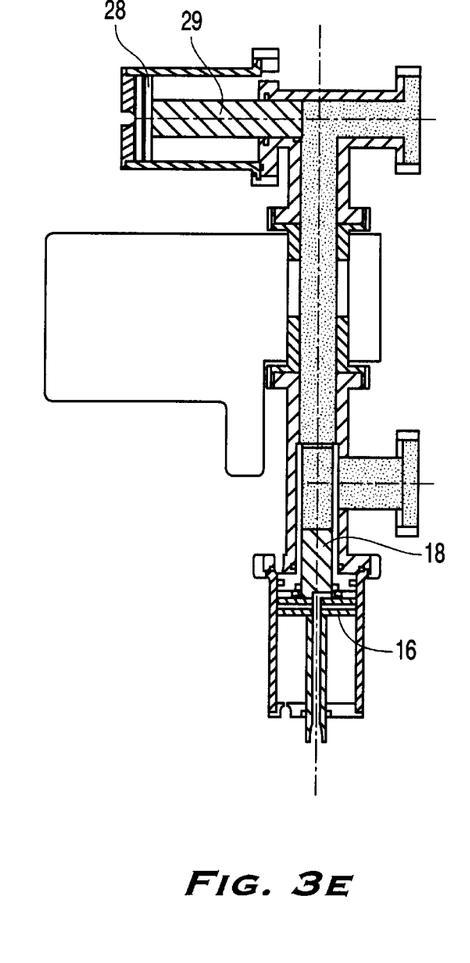
Figure 3F:
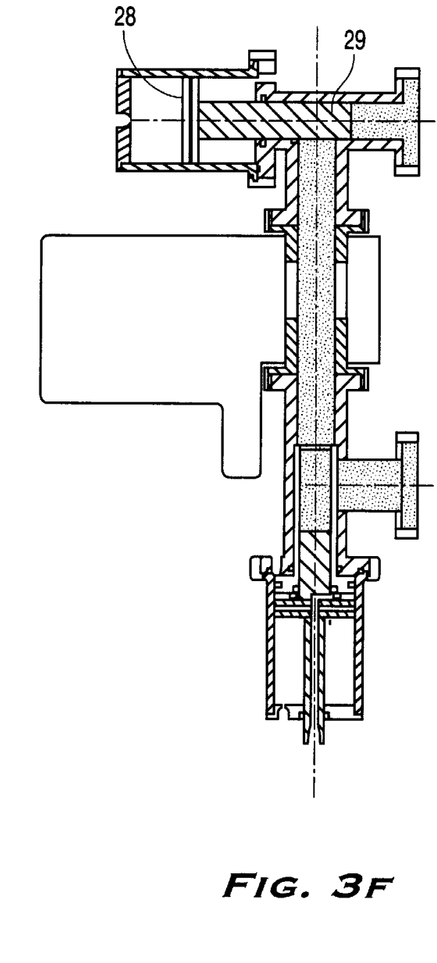

The measuring equipment in FIG. 3d will now be described in more detail. It comprises a wide-spectrum light source 32 emitting light within the working region, in the present case the near-infra-red region between 700 and 1200 nm. The present embodiment comprises a tungsten-halogen lamp emitting a major proportion of the electrical energy supplied in the infra-red spectral region and having a wattage between 20 and 70W.

Close to the light source 32, a preferably elliptical reflector 33 is placed in such a manner, that the light will mainly be directed towards the right. A rotatable filter disc 34 is placed between the light source 32 and the window 24 in the tube section 10*b*, said disc comprising between 6 and 20, e.g. 12, different filters 35, each allowing passage of light at a respective wavelength through the windows 24 in the tube section 10*b*. The monochromatic light entering through the left-hand window will suffer substantial loss during the passage through the material in the tube, leaving the tube through the right-hand window to strike a wide-spectrum photo-detector 36, e.g. an Si wafer.

The attenuation of the light in the material is due to the absorption caused by the various components in the material as well as the dispersion and reflection of light caused by phase transitions or particles in the material. The absorption depends on the components and the wavelength.

Thus, the photo-detector 36 will produce signals depending on the content of components in the material being examined and the wavelength. The signal is amplified, filtered, digitized and stored in an electronic memory. The windows and the path of the light beam are dimensioned in such a manner, that the detector 36 receives light having passed through a volume of material of more than 100 ml. The volume of material corresponds to the volume of the space between the windows 24.

The measuring equipment comprises a step motor 37 for rotation of the filter disc 34 to bring the filters 35 one by one into the path of the light beam between the light source 32 and the detector 36. Each time a new filter has been placed in a measuring position, the signal from the detector 36 will be registered and stored, the strength of this signal depending on the absorption of the material concerned in the wavelength region of the filter. When measuring values have been registered and stored for all filters in the disc 34, the measuring process is complete. The removal of material from the region between the windows 24 can then be initiated by opening the top of the vertical part of the tube.

Figure 4:
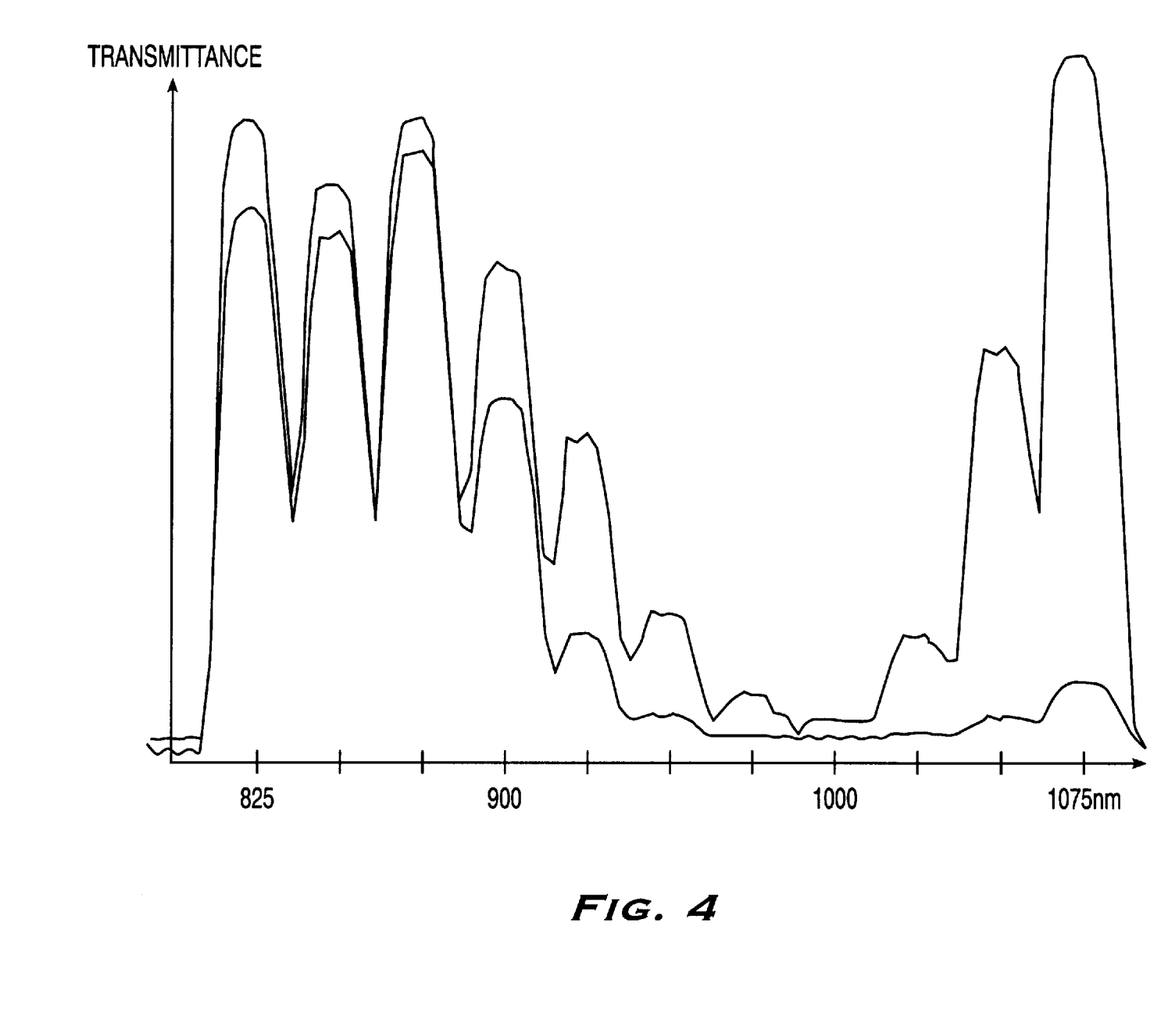
FIG. 4 shows the transmittance at various discrete wavelengths of samples of meat containing much and little fat as measured in the measuring equipment.

FIG. 4 shows the signal from the detector 36 during one rotation of the filter disc 34. The upper curve represents a finely minced sample of pork meat with a fat content of approx. 50%. The sample is placed in the tube segment 10*b*. The lower curve has been recorded with a finely minced sample of beef with approx. 5% fat. The samples attenuate the light approx. 4000 times. The peak values of the curves represent the transmittance at the 11 different wavelengths. It will be seen that the samples attenuate the light differently at the different wavelengths due to the different content of fat and water in the samples, this being used for calculating these values.

By means of the measuring values stored, the data unit 6*a* will automatically compute the content of e.g. fat in the material, a program with the necessary computing routines having been read into the unit. When working with coarsely comminuted meat material as described, a single result is not sufficiently reliable, and for this reason it is necessary to repeat the sampling and measuring cycle a number of times, e.g. 10 times, until it is possible to compute a sufficiently reliable value of the fat content on the basis of the sum total of the measurement values or results.

If the material is homogeneous, e.g. in the case of finely comminuted meat or meat emulsions, satisfactorily accurate results may be achieved already by carrying out a single measuring cycle.

Using the stored measuring values, it is possible to determine the content of various components in the material, e.g. fat, protein, collagen and water. If a number of sets of measuring values produced from respective sampling and measuring cycles are used, a substantial improvement of the accuracy of the results will be achieved, this especially being of importance when the portion being measured in each cycle is not representative.

Further, the measurement values from each sampling and measuring cycle may be used for ascertaining whether the mixing procedure is carried out in an optimal manner. Thus, the fat content of the material may be computed for each sampling and measuring cycle, and the result compared to the previous result or the average of a number of immediately preceding results. If a large deviation is found, this signifies that the material in the tank is still inhomogeneous and that the mixing operation is to be continued. If the deviation is only quite small or below a certain limiting value, the homogeneity of the material cannot be improved by continuing the mixing operation, for which reason this operation is terminated. In this manner, it is normally possible to reduce the duration of the mixing operation to the strictly necessary, and the further mechanical working of the material is avoided.

Instead of the deviation, it is possible to use the standard deviation of the results for controlling the duration of the mixing operation. If the computed standard deviation for the most recent cycles falls below a certain level, or if it is not improved by continuing the mixing operation, this signifies that the mixing operation is to be terminated.

Already before the material has become as homogeneous as desired, it is possible in many cases to determine the fat content or the like with a satisfactory accuracy, e.g. on the basis of the tendency of the results to approach a final value. Thus, it can be possible relatively early in the mixing operation to predict the amount of fat-containing meat to be added to the material in the tank to make the material resulting from the complete mixing process comply with the specifications. Because of this, the method and the plant make it possible to adjust the composition of the material rapidly, this contributing to ensure that the material is not subjected to mechanical working longer than what is necessary to achieve a homogeneous mixture. When, by means of the measurements, it is possible to ascertain that the material in the tank exhibits the desired homogeneity, a final check of the fat content may be made on the basis of the measurement results from the most recent measuring cycles.

Obviously, it is possible to adjust the composition of the material concurrently during the mixing operation by adding fat-containing material, making it possible for the end product to comply with strict specifications or be close to an optimal fat-content within given specifications without necessarily increasing the mixing time. The adding of fat-containing material in connection with the adjustment may be carried out manually or automatically.

All these computations and evaluations may be carried out automatically by the data unit 6*a* on the basis of the measurement data received. When, aided by a program having been read in, this unit e.g. ascertains that the results are stable, it can automatically send a signal to the control panel 6 that the mixing operation is completed with regard to homogeneity, after which the control panel 6 itself or an operator receiving a signal from the panel can stop the motor arrangement driving the mixing devices.

In the present embodiment measurements are carried out using near-infra-red radiation. The material being advanced in the tube 10 may, however, be examined using other types or a number of different types of electromagnetic energy. E.g. downstream of the tube segment 10*b*, a further tube segment may be inserted having measuring devices for determining the material's content of water in the liquid phase by means of microwave energy. In this case, the material's ice content may be determined as the difference between the water percentage determined with near-infrared measurement in the tube segment and the water percentage being determined using microwaves.

Figure 5:
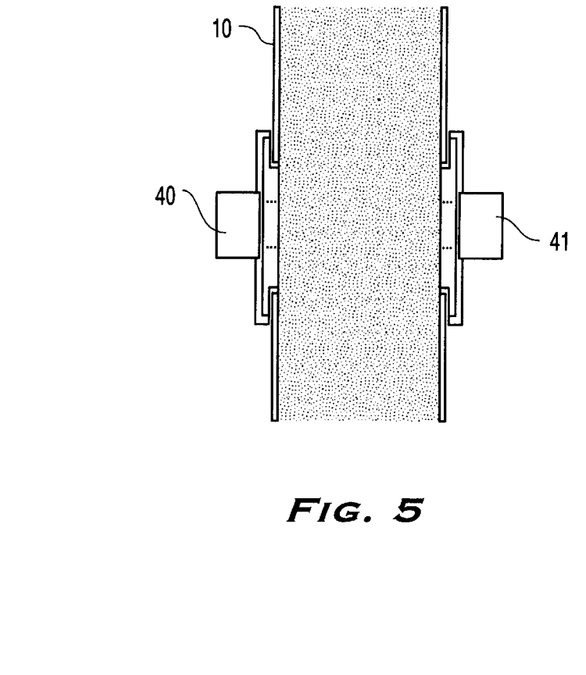
FIG. 5 shows another embodiment of the measuring equipment in the apparatus according to FIGS. 3a–3f.

Instead of a wide-spectrum light source behind a filter disc it is possible to use discrete monochromatic light sources, each admitting light at a respective wavelength. FIG. 5 shows such an embodiment, utilizing laser diodes instead of the lamp and the filter disc. The embodiment of FIG. 5 possesses the advantage of having no moving parts.

The embodiment comprises a series of (high-power) laser diodes 40, each radiating light of a predetermined wavelength inwards against the material sample. Typically, 4–20 diodes situated on the same chip, are used. Each laser diode emits light of a unique wavelength within the region 800–1050 nm, making it unnecessary to use filters. For measuring the light having passed through a sample of a thickness 5–10 cm, a PMT detector 41 is used. By activating one of the diodes 40 at a time, the detector 41 is used to measure how much light penetrates the sample at the various wavelengths.

Figure 6:
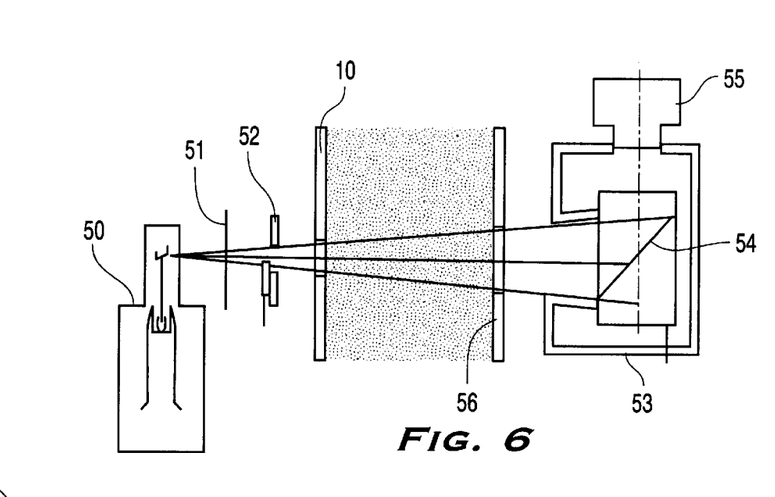
FIG. 6 shows a third embodiment of the measuring equipment.

FIG. 6 shows an embodiment of a measuring device based on the use of X-rays. The measuring device comprises an X-ray source 50 of 50 kV, a filter 51 and an adjustable aperture 52. Further, the device comprises a radiation-receiving part in the form of a radiation trap 53 and a detector 54, of which the latter may be a usual detector or a fluorescent screen, the light emitted by the latter being registered by a CCD camera 55. The tube 10 comprises two beryllium windows 56 allowing passage of X-rays. The thickness of the meat raw material in the tube 10 is e.g. 6 cm. The material is compressed under a pressure of 13 bar, so that in practice it may be regarded as a mixture without air pockets. At this pressure, more than 3% air in the mixture is needed to cause a measuring error of more than 0.5%.

The focus-detector distance of the X-ray source 50 is 25 cm, and after passing through the 6 cm of meat material, the radiation has a strength of approx. 1.6 mGy/mA min., which may be measured with a good degree of certainty. The uncertainty where measuring with a 10×10 mm detector is 0.01% when measuring in 1 second, which means that the measuring uncertainty is insignificant. (The variation when determining fat percentage is a different matter, as in this case, the physical properties of the material will be important.).

The equipment may also be used for measuring partially frozen goods without substantial changes in the measurement results. If, however, measurements are carried out on salted raw materials, an increased attenuation of the X-ray radiation will occur corresponding to an increase of 1% of the meat percentage for each percent by weight in NaCl. For this reason, the percentage of salt must be approximately known in this case.

Figure 7:
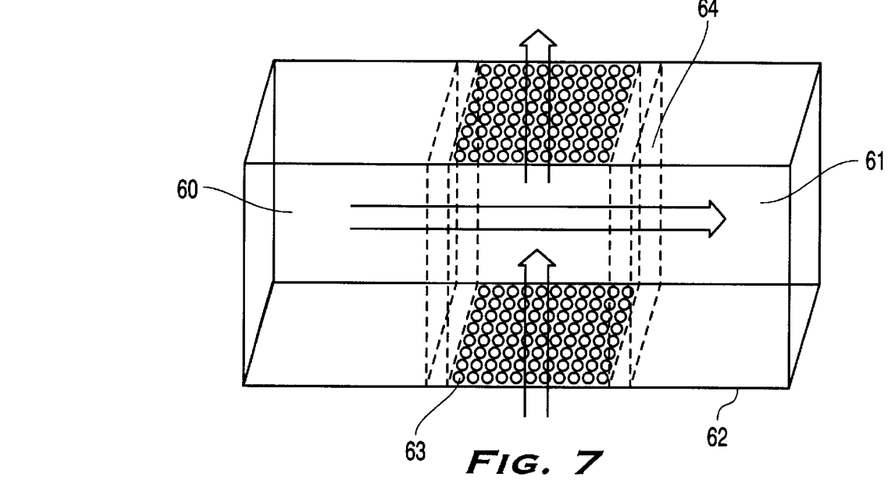
FIG. 7 shows a fourth embodiment of the measuring equipment.

FIG. 7 shows a measuring device for measuring properties of material in the tube 10 by means of microwaves. The device comprises a microwave generator 60, a microwave detector 61 and a waveguide 62 having a cage 63 between the generator 60 and the detector 61. The holes in the cage 63 have a diameter of e.g. 10% of the wavelength being used, so that the microwaves cannot escape from the waveguide 62. The diameter of the holes is preferably at least equal to the size of the particles in the coarsely comminuted meat material. The meat material is forced through the cage 63 in the vertical direction as indicated by the arrows. Glass windows 64 aligned with the walls of the tube 10 prevent the material from entering the regions of the generator and the detector. The glass windows 64 cause practically no attenuation of the microwaves passing through them.

The microwave generator 60 emits energy at a fixed frequency and a constant power of 1–10 mW. The energy being received by the microwave detector 61 will vary with the fat content in the material between the windows 64 and will be transformed into a voltage being transmitted to the data unit 6a for further processing.

The measuring equipment has a high capacity.

EXAMPLE 1

Necessary Repetition Factor for Representative Sample

In order to provide the requisite accuracy when determining the content of fat, protein, water, etc., it is necessary to ascertain whether the quantity being taken out as a sample in each cycle is representative of the total quantity of meat in the mixing tank and, if this is not the case, how many times the cycle is to be repeated to achieve values that are representative of the total quantity of meat (e.g. 1200 kg).

For examining this relationship a program has been developed to simulate the taking of samples from the mixing tank. The program is based on a number of assumptions about the nature of the coarsely comminuted meat in the mixing tank and about the size of the sample relative to the total quantity of meat. The following assumptions are used in the program:

total quantity of meat in the tank: 1000 kg weight of sample: 0.5, 1, 2, 5 and 10 kg meat comminution degree: cubes with sides measuring 10 and 20 mm, respectively (corresponding to a particle volume of 1 and 8 $cm^3$, respectively)

average fat content: varying between 10 and 50% variation in cube volume: 20% of the average cube volume, i.e. that 95% of all 1 $cm^3$ cubes lie between 0.4 and 1.6 $cm^3$ variation in fat content from cube to cube: 20%, but min. 0.8% fat and max. 85% fat, i.e. that in a mixture with 30% fat, 97.5% of all cubes lie between 0.8 and 70% fat air volume: 0%

The program functions in the manner that the sample volume and the volume of material in the tank are composed of cubes selected at random on the basis of the above parameters. Then, the fat content in the sample volume may be compared to the fat content of the material in the tank for different average fat percentages, sample sizes and degrees of coarse comminution.

The table below indicates the RSD (residual standard deviation) for various sample sizes and degrees of coarse comminution. The results have been produced by letting the computer carry out ten samplings from each of six mixtures with a fat content varying from 10 to 50%. RSD is a measure of the average deviation between the fat content in the sample and in the material in the tank.

| Coarse comminution (mm) | Sample size (kg) | RSD (% abs.) |
|---|---|---|
| 10 × 10 × 10 | 10 | 0.11 |
|  | 5 | 0.19 |
|  | 2 | 0.33 |
|  | 1 | 0.43 |
|  | 0.5 | 0.81 |

-continued

| Coarse comminution (mm) | Sample size (kg) | RSD (% abs.) |
|---|---|---|
| 20 × 20 × 20 | 10 | 0.61 |
|  | 5 | 0.73 |
|  | 2 | 1.30 |
|  | 1 | 1.39 |
|  | 0.5 | 2.3 |

A coarse comminution down to cubes of 10×10×10 mm gives an RSD at 5 kg that is less than the error when measuring fat content in the laboratory. With a coarse comminution down to cubes of 20×20×20 mm it is necessary to take a sample of substantially more than 10 kg to make the error less than the laboratory error.

The results may also be read in the following manner: If a perfect method of analysis is available, capable of determining the fat content of the sample volume, the fat content having been determined will in 95% of the cases differ less than twice the RSD value from the fat content in the tank. With a sample size of 5 kg of cubes 10×10×10 mm, the variation will be greater than 0.38% in only 5% of the cases; this is fully acceptable with a certainty of the analysis method of 0.5%.

If measurements are carried out in the plant on 125 ml material in each cycle, these conditions will make it necessary to carry out 40 sampling and measuring cycles to obtain a representative value of e.g. the fat content in the mixing tank with a certainty of analysis of 0.5%. If a somewhat reduced certainty can be accepted, the number of cycles may be reduced, e.g. to 10.

EXAMPLE 2
NIT Measurements on Pork with Varying Fat Content and Degree of Coarse Comminution The tests are to ascertain whether an NIT analysis requires a complete comminution before measurements are carried out on the material.

2.5 kg of each of the following products are procured from a slaughterhouse: foreloin (fat content 9%), neck (fat content 24%) and shoulder cuts (fat content 45%). These test portions are coarsely comminuted to 13 mm by means of a cutter.

From each of the test portions 400 g are taken out and measured on an NIT analysis instrument for laboratory use (model Infratec 1255 from Tecator). The NIT-instrument comprises five cups with sample material. The effective sum total of the sample volume for the five cups is 25 ml. Then, the material having been removed is returned to the test portions and the latter comminuted to 10 mm. From each type of test portion partial samples of 400 g are taken out and measured on the NIT instrument. Further, the procedure is repeated to provide measurements on meat material of 8.5 and 3 mm. Finally, the test portions are analysed for fat content using traditional laboratory analysis.

Figure 8:
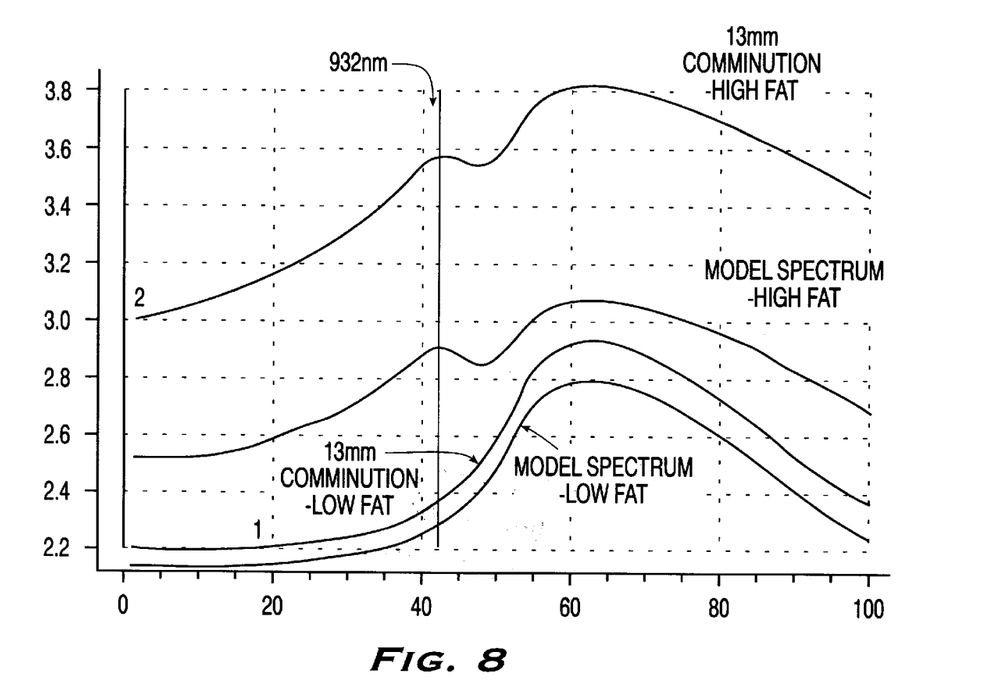
FIG. 8 shows NIT spectra of two types of meat in two different degrees of comminution.

FIG. 8 shows two average spectra for shoulder cuts and foreloin comminuted to 13 mm as well as two previously produced model spectra for meat of 3 mm with similar fat content.

It can be seen from the Figure that spectra with the same percentage of fat mainly differ only by the parallel displacement along the Y-axis; this is of no importance for determining the fat content, since this solely requires the use of the relative changes at the various wavelengths. It can also be seen that the absorption at 932 nm provides a clear indication of the fat content of the sample.

Figure 9:
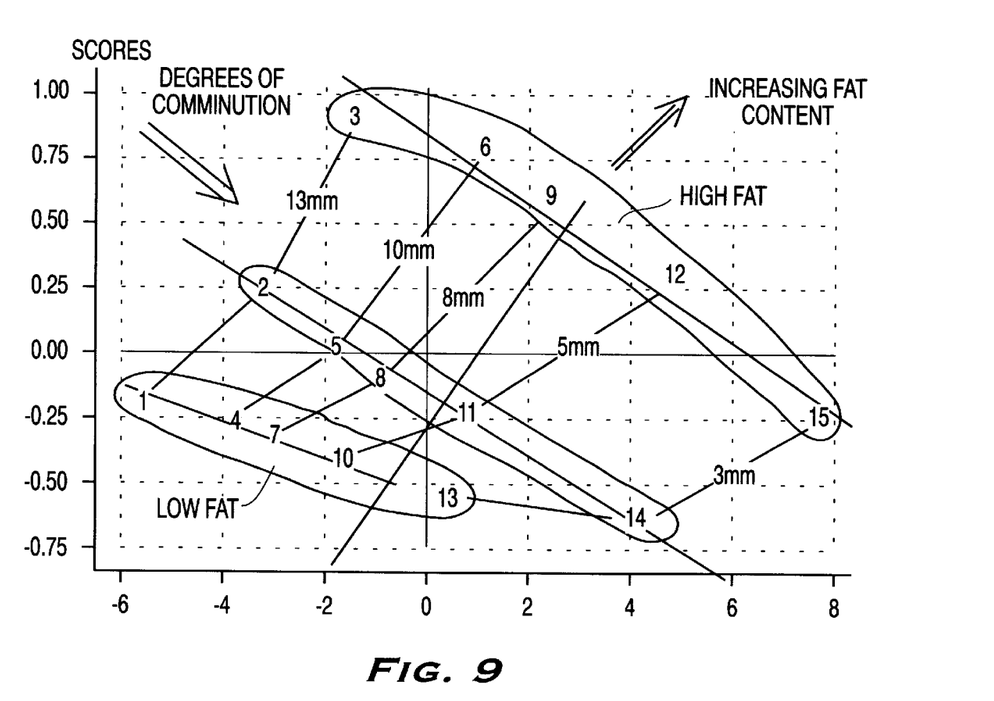
FIG. 9 is a classification diagram based upon a principal component analysis of average spectra.

The next step is to carry out a principal-component analysis (PCA) of the average spectra for each of the three types of meat and each of the five degrees of comminution, so that a total of 15 spectra enter into the analysis. The result of this classification is shown in FIG. 9.

It will be seen that the spectra form groups in two directions, viz. a first direction indicating the fat content of the sample, and a second direction approximately at right angles to the first direction and indicating the degree of comminution. Thus, the Figure shows that it is possible using NIT analysis to determine both the fat content and the degree of comminution.

The invention has been explained in the above mainly with reference to the mixing of meat products, but it will be understood that the invention may be used for measuring mixtures of materials, with which electromagnetic radiation may be used to provide measuring results containing information about the state of the mixture.

What is claimed is:

1. A method of mixing a flowable material, which comprises:

a) placing at least one unhomogeneous food, fodder or pharmaceutical material having a form or size that can lead to uneven component measurement into a tank provided with mixing devices;

b) measuring and registering the content of at least one component from samples taken from the material in the tank by removing material from the tank through a tube which is situated adjacent the tank and which communicates with the internal space of the tank;

c) moving the removed material to a segment of the tube adapted for making measurements;

d) measuring the effect caused by the material placed in said tube segment on electromagnetic energy made to enter the tube while the material is retained therein;

e) repeating steps c–d, optionally while introducing completely or partly new material in the tube segment; and f) registering at least one measurement value from the individual measuring procedure to determine the content of the components to be mixed.

2. The method according to claim 1 wherein the content of at least one component of the material in the tank is determined by repeating steps c–d after introducing new material into the tube segment, and repeating the process until a representative sample is tested.

3. The method according to claim 1 wherein the material is introduced into the tube segment, and is returned to the tank at a distance from the opening serving for removing material from the tank after analysis.

4. The method according to claim 1 wherein steps c–d are carried out while the material is being mixed in the tank.

5. The method according to claim 1 wherein the material is brought to rest in the tube segment prior to carrying out the measurement.

6. The method according to claim 1 wherein the material present in the tube segment is compressed before the measurement is carried out.

7. The method according to claim 1 wherein at least one form of electromagnetic energy comprising microwaves of frequencies in the interval between about 300 MHz and about 300 Ghz, single-energy, dual energy or multi-energy, X-ray, or near-infra-red radiation is used.

8. The method according to claim 7 wherein, if microwaves are used, the tube segment is configured in the shape of a microwave guide, and then one of attenuation, phase shift or time delay of the microwaves is measured in the tube segment, if X-rays are used, then attenuation of X-ray radiation transversely through a material contained in the tube segment is measured, or if near-infra-red radiation is used, then transmittance or absorbance of a material contained in the tube segment is measured in the near-infra-red interval (NIT).

9. The method according to claim 8 wherein measuring of the transmittance or absorbance of the material placed in the tube segment is conducted at a number of wavelengths in the interval between about 700 and about 2400 nm; and the content of at least one of the measuring values is registered.

10. The method according to claim 1 wherein the measuring values are used to ascertain when the mixture in the tank is sufficiently homogenous to allow the mixing process to be terminated and the material discharged from the tank or subjected to a succeeding processing step.

11. The method according to claim 1 wherein the content of at least one component of the material is determined on the basis of at least one of the registered measuring values, and the results are shown on a display unit or used for controlling a dosage control unit associated with the tank and adapted to add a quantity of a component to the material in the tank.

12. The method according to claim 1 wherein, the transmittance or absorbance of a particulate material with an average particle size between 2 and 30 mm, is measured at a number of wavelengths in the near-infra-red interval, after which at least one of the registered measuring values is used to determine at least one of:

the content of at least one component of the material; or the sufficiency of homogeneity of the mixture in the tank with regard to at least one component such that the mixing process can be terminated and the material discharged from the tank or subject to a succeeding processing step.

13. A plant for mixing an inhomogeneous flowable food, fodder or pharmaceutical material, comprising: a tank (2) for combining the material, a plurality of mixing devices (4), an examining unit adjacent the tank and comprising a tube (10) having an opening communicating with the internal space of the tank (2) for removing material from the latter, in said tube (10), a movable closure member (17) situated in said tube adjacent the opening for receiving material, a conveying member (18) for conveying material having been removed through said opening into a segment (10b) of said tube (10) adapted for carrying out measurements, a measuring device (32–37; 40, 41; 50–56; 60–64) situated adjacent said segment (10b) of said tube (10) and adapted to transmit electromagnetic energy into said segment and to measure the influence on this energy exerted by the material being present in said segment, a control unit (6a) to cause the measuring procedure comprising the introduction of completely or partly new material in said segment (10b) and measuring of its influence on electromagnetic energy, to be repeated, and a recording unit connected to said measuring device and adapted to record individual measurement values or sets of same for material having been measured in the respective measuring procedures.

14. Plant according to claim 13, characterized in that said measuring device comprises a light source (32,40) on one side of said tube segment (10b) and a light receiver (36,41) on the opposite side, and that the walls of the tube segment (10b) lying in the path of rays between the light source and the light receiver consist of a material (24) that is translucent for the wavelength interval of the light to be examined, depending on the flowable material, on which measurements are to be carried out.

15. Plant according to claim 14, characterized in that the light source (32) and the light receiver (36) are of the wide-spectrum type, and that a rotatable filter disc (34) is placed in the ray path between the light source and the light receiver, said filter disc (34) having a number of filters (35) situated at equal distances from the axis of rotation of the disc and each adapted to allow rays of a respective wavelength interval to pass, a motor (37) on the shaft of said disc (34) being adapted to bring one filter at a time into the path of rays.

16. Plant according to claim 14, characterized in that a number of monochromatic light sources (40), each adapted to emit light in a respective wavelength interval, is situated on one side of said tube segment (10b), and that a light receiver (41) is situated on the opposite side of said tube segment.

17. Plant according to claim 16, characterized by between 4 and 20 monochromatic light sources (40) in the form of laser diodes are situated on one side of said tube segment (10b) and adapted to emit light, each in a respective wavelength interval within the region between 700 and 1200 nm.

18. Apparatus according to claim 13, characterized in that said closure member (17) is adapted to be opened in connection with the reception of material and to be closed in connection with the conveying of material having been received into said tube segment (10b) adapted for carrying out the examination.

19. Apparatus according to claim 13, characterized by a second closure member (29) in the tube (10) on the side of said tube segment (10b) opposite said receiving opening, said second closure member (29) being adapted to be closed for a period while the conveying member (18) conveys fully or partly new material into said tube segment (10b) adapted for carrying out the examination, and to open when the material having been examined is to be moved out of said tube segment (10b).

20. Apparatus according to claim 13, characterized in that said conveying member is a plunger (18) slidable in a fluid-tight manner along the inside of said tube (10).

21. Apparatus according to claim 13, characterized by comprising one or a number of pneumatic cylinders (14,27) with associated pistons (15,16,28) adapted to actuate said conveying member (18) and/or closure members (17,29) in said tube (10).

22. A method of mixing flowable material comprising:
a) placing at least one unhomogeneous food material, fodder material or pharmaceutical material in a tank provided with mixing devices;
b) measuring and registering the content of at least one component in samples taken from the material in the tank;
c) removing material from the tank through a tube which is situated adjacent the tank and which communicates with the internal space of the tank;
d) moving the material to a segment of the tube adapted for making measurements, where the measurement is carried out while the material in the tube is at rest;
e) measuring the effect caused by the material placed in said tube segment on electromagnetic energy made to enter the tube;
f) repeating the above steps c–e, optionally with the introduction of completely or partly new material in the tube segment; and
g) registering at least one measurement value from the individual measuring procedure.

23. A method of mixing flowable material comprising:
a) placing at least one unhomogeneous food material, fodder material or pharmaceutical material in a tank provided with mixing devices;

b) measuring and registering the content of at least one component in samples taken from the material in the tank;

c) removing material from the tank through a tube which is situated adjacent to the tank and which communicates with the internal space of the tank;

d) moving the material to a segment of the tube adapted for making measurements;

e) compressing the material present in the tube segment to a pressure of between about 200 and about 2000 kPa (about 2 and about 20 bar);

f) measuring the effect caused by the material placed in said tube segment on electromagnetic energy made to enter the tube;

g) repeating the above steps c–e, optionally with the introduction of completely or partly new material in the tube segment; and h) registering at least one measurement value from the individual measuring procedure.

* * * * *